United States Patent
Yang et al.

(10) Patent No.: US 12,084,412 B2
(45) Date of Patent: Sep. 10, 2024

(54) SYNTHESIS OF TRIFLUOROACETYL IODIDE (TFAI) FROM TRIFLUOROACETYL CHLORIDE (TFAC) AND HYDROGEN IODIDE (HI) IN A LIQUID PHASE REACTION

(71) Applicant: Honeywell International Inc., Charlotte, NC (US)

(72) Inventors: Terris Yang, East Amherst, NY (US); Haiyou Wang, Amherst, NY (US)

(73) Assignee: Honeywell International Inc., Charlotte, NC (US)

(*) Notice: Subject to any disclaimer, the term of this patent is extended or adjusted under 35 U.S.C. 154(b) by 157 days.

(21) Appl. No.: 17/219,390

(22) Filed: Mar. 31, 2021

(65) Prior Publication Data

US 2021/0317062 A1    Oct. 14, 2021

Related U.S. Application Data

(60) Provisional application No. 63/007,220, filed on Apr. 8, 2020.

(51) Int. Cl.
| | | |
|---|---|---|
| C07C 51/58 | (2006.01) |
| B01J 19/00 | (2006.01) |
| B01J 21/06 | (2006.01) |
| B01J 21/18 | (2006.01) |
| B01J 29/035 | (2006.01) |
| B01J 27/224 | (2006.01) |

(52) U.S. Cl.
CPC ............ C07C 51/58 (2013.01); B01J 19/004 (2013.01); B01J 21/06 (2013.01); B01J 21/18 (2013.01); B01J 29/035 (2013.01); *B01J 27/224* (2013.01); *B01J 2219/00029* (2013.01); *B01J 2219/00033* (2013.01)

(58) Field of Classification Search
None
See application file for complete search history.

(56) References Cited

U.S. PATENT DOCUMENTS

| | | | |
|---|---|---|---|
| 5,892,136 | A | 4/1999 | Nagasaki et al. |
| 2006/0122440 | A1 | 6/2006 | Mukhopadhyay et al. |
| 2012/0190892 | A1 | 7/2012 | Saint-Jalmes et al. |
| 2020/0062679 | A1 | 2/2020 | Nair et al. |

FOREIGN PATENT DOCUMENTS

| | | |
|---|---|---|
| CN | 103524325 A | 1/2014 |

OTHER PUBLICATIONS

Haszeldine ("124. The Reactions of Metallic Salts of Acids with Halogens. Part I. The Reaction of Metal Trifluoroacetates with Iodine, Bromine, and Chlorine" J. Chem. Soc. 1951, p. 584-587) (Year: 1951).*

(Continued)

*Primary Examiner* — Amy C Bonaparte
(74) *Attorney, Agent, or Firm* — Faegre Drinker Biddle & Reath LLP (57) ABSTRACT

The present disclosure provides a process for making trifluoroacetyl iodide (TFAI) in a liquid phase reaction. Specifically, the present disclosure provides a liquid phase reaction of trifluoroacetyl chloride (TFAC) and hydrogen iodide (HI), with or without a catalyst, to form trifluoroacetyl iodide (TFAI). The reaction may be performed at ambient or elevated temperatures.

15 Claims, 13 Drawing Sheets

(56) References Cited

OTHER PUBLICATIONS

Hydriodic Acid National Center for Biotechnology Information (2023). PubChem Compound Summary for CID 24841, Hydriodic acid. Retrieved Jan. 12, 2023 from https://pubchem.ncbi.nlm.nih.gov/compound/Hydriodic-acid.https://pubchem.ncbi.nlm.nih.gov/compound/24841) (Year: 2023).*

Trifluoroacetyl Chloride (National Center for Biotechnology Information (2023). PubChem Compound Summary for CID 61106, Trifluoroacetyl chloride. Retrieved Jan. 12, 2023 from https://pubchem.ncbi.nlm.nih.gov/compound/Trifluoroacetyl-chloride) (Year: 2023).*

Cantillo ("Halogenation of organic compounds using continuous flow and microreactor technology" React. Chem. Eng. 2017, 2, p. 7-19). (Year: 2017).*

International Search Report and Written Opinion received for PCT Patent Application No. PCT/US2021/025961, mailed on Jul. 27, 2021, 11 pages.

* cited by examiner

SYNTHESIS OF TRIFLUOROACETYL IODIDE (TFAI) FROM TRIFLUOROACETYL CHLORIDE (TFAC) AND HYDROGEN IODIDE (HI) IN A LIQUID PHASE REACTION

CROSS-REFERENCE TO RELATED APPLICATION

This application claims priority to Provisional Application No. 63/007,220, filed Apr. 8, 2020, which is herein incorporated by reference in its entirety.

FIELD

The present disclosure provides a process for producing trifluoroacetyl iodide (TFAI) in a liquid phase reaction from trifluoroacetyl chloride (TFAC) and hydrogen iodide (HI), with or without a catalyst.

BACKGROUND OF THE DISCLOSURE

Trifluoroiodomethane ($CF_3I$) is an iodofluorocarbon (IFC). IFCs consist mainly of carbon, fluorine, and iodine and have been identified as attractive potential replacements for chlorofluorocarbons (CFCs) and hydrochlorofluorocarbons (HCFCs). Broadly, IFCs, especially those containing just one iodine atom are non-flammable, have low boiling points, high volatilities, low viscosities, and low surface tensions, making them attractive alternative candidates as non-aqueous solvents for replacement of CFCs and HCFCs. Although iodine-containing organic compounds tend to be toxic, reactive, and chemically unstable the presence of the fluorine atoms bonded to the iodinated carbon atom offers considerable improvements in stability and greatly reduces toxicity. $CF_3I$ is non-flammable, has very low acute toxicity, extremely low Global Warming Potential (GWP) and negligible Ozone Depleting Potential (ODP). In addition, $CF_3I$ readily undergoes photolysis when exposed to UV radiation in the tropospheric layer of the atmosphere, and thus never reaches the stratosphere. The short atmospheric life cycle of $CF_3I$ accounts for its extremely low GWP and negligible ODP. Besides these properties, $CF_3I$ is miscible with mineral oil and is also compatible with refrigeration system materials making it an acceptable environmentally benign candidate for applications in refrigeration, fire suppression, aerosol propellants, foam blowing, air conditioning, heat transfer media, and gaseous electrolytes.

With increasing mandates that require the phase down of high GWP products, an important objective of the Heating, Ventilation and Air Conditioning (HVAC) industry has been to develop a replacement for the industry standard refrigerant R410A. R410A is a near-azeotrope blend of difluoromethane (HFC-32) and pentafluoroethane (HFC-125) that is flammable, does not contribute to ozone depletion, and has high GWP.

A favorable process for making $CF_3I$ is to use trifluoroacetyl chloride (TFAC) and hydrogen iodide (HI) as starting materials to make the intermediate product trifluoroacetyl iodide (TFAI) which can be used to make $CF_3I$ in the next step reaction.

The present disclosure provides processes for producing trifluoroacetyl iodide (TFAI) from trifluoroacetyl chloride (TFAC) and hydrogen iodide (HI) in liquid phase reaction with or without catalyst at ambient or elevated temperatures.

SUMMARY

The present disclosure provides a process for making trifluoroacetyl iodide (TFAI) in a liquid phase reaction. Specifically, the present disclosure provides a liquid phase reaction of trifluoroacetyl chloride (TFAC) and hydrogen iodide (HI), with or without a catalyst, to form trifluoroacetyl iodide (TFAI). The reaction may be performed at ambient or elevated temperatures.

The present disclosure provides a process for producing trifluoroacetyl iodide (TFAI) in a liquid phase reaction comprising the steps of providing trifluoroacetyl chloride, hydrogen iodide, and an optional catalyst, and reacting the trifluoroacetyl chloride and hydrogen iodide in a liquid phase reactor to produce trifluoroacetyl iodide.

The mole ratio of trifluoroacetyl chloride to hydrogen iodide may be from about 1:10 to about 10:1.

The weight ratio of the catalyst to the trifluoroacetyl chloride may be from about 0.001:1 to about 0.5:1.

The catalyst may be selected from the group consisting of silicon carbide, activated carbon, carbon molecular sieves, and combinations thereof.

The liquid phase reaction of the trifluoroacetyl chloride, the hydrogen iodide, and the optional catalyst may be conducted at a temperature from about 0° C. to about 200° C.

The present disclosure further provides a process for producing trifluoroacetyl iodide (TFAI) in a liquid phase reaction, the process comprising mixing trifluoroacetyl chloride, hydrogen iodide, and an optional catalyst, and reacting the trifluoroacetyl chloride, hydrogen iodide and an optional catalyst in a liquid phase reactor to produce trifluoroacetyl iodide and hydrogen chloride.

The process may further include separating the trifluoroacetyl iodide from the hydrogen chloride.

The process provided by the present disclosure may be a continuous process.

The process provided by the present disclosure may be a batch process.

DETAILED DESCRIPTION

The present disclosure provides a liquid phase process for producing trifluoroacetyl iodide (TFAI) via the reaction shown below in Equation 1.

$$CF_3COCl + HI \rightarrow CF_3COI + HCl \quad \text{Equation 1:}$$

The liquid phase process can be conducted in a liquid phase reactor with or without agitation. Preferably, the reactor is equipped with an agitator, and the reactor may be formed in whole or in part of materials including Hastelloy C 276, Inconel 600, Inconel 625, Monel 400, SS316, SS316L, PFA lined, PTFE lined, glass lined etc.

The reaction can be run under conditions effective to form trifluoroacetyl iodide (TFAI) but not $CF_3I$ to avoid the difficulties arising from the separation of trifluoroacetyl chloride (TFAC) from $CF_3I$.

The reaction temperatures may be as low as about 0° C., about 25° C., about 35° C., about 40° C., about 50° C., or as high as about 60° C., about 90° C., about 120° C., about 150° C., or about 200° C., or within any range defined between any two of the foregoing values.

The pressure may be as low as about 5 psig, about 25 psig, about 50 psig, about 100 psig, about 150 psig, about 200 psig, about 250 psig, or as high as about 300 psig, about 350 psig, about 400 psig, about 450 psig, about 500 psig, or within any range defined between any two of the foregoing values.

The TFAC:HI (trifluoroacetyl chloride:hydrogen iodide) ratio may be as low as about 1:10, about 2:1, about 3:1, about 4:1, or as high as about 5:1, about 6:1, about 7:1, about 8:1, about 9:1, or about 10:1, or within any range defined between any two of the foregoing values. Preferably, the TFAC:HI ratio is from 1:2 to 2:1, such as 1:1, 1:1.5, 1:1.9, 1.1:1, 1.5:1, 1.9:1, for example. More preferably, the TFAC/HI ratio is from 1:1 to 2:1.

A catalyst may be added to the reaction. The catalyst may be silicon carbide, activated carbon, carbon molecular sieves, or combinations thereof. The weight ratio of the catalyst to TFAC may be as low as about 0.001:1, about 0.01:1, about 0.02:1, about 0.03:1, about 0.04:1, or as high as about 0.05:1, about 0.06:1, about 0.07:1, about 0.08:1, about 0.09:1, about 0.1:1, about 0.2:1, about 0.5:1, or within any range defined between any two of the foregoing values.

The residence time may be as low as about 0.1 hour, about 0.5 hour, about 1 hour, about 5 hours, about 10 hours, about 15 hours, or as high as about 20 hours, about 30 hours, about 40 hours, about 50 hours, or within any range defined between any two of the foregoing values.

The reaction can be carried out in a batch-wise or continuous mode. Preferably, the reaction is carried out in a continuous mode.

The reactor may be equipped with a distillation column to remove low boiling by-products, such as HCl. As reaction progresses, the TFAI concentration rises in the reactor and a liquid stream can be drawn continuously or intermittently for product separation. The isolated TFAI can be sent to a storage tank for the use in next step reaction as raw material to make $CF_3I$, while the separated TFAC and/or HI can be recycled back to the reactor.

EXAMPLES

In the following examples, the manufacture of TFAI from TFAC and HI in a liquid phase process is demonstrated.

Example 1

Liquid Phase Synthesis of Trifluoroacetyl Iodide (TFAI) at Ambient Temperature

Figure 1:
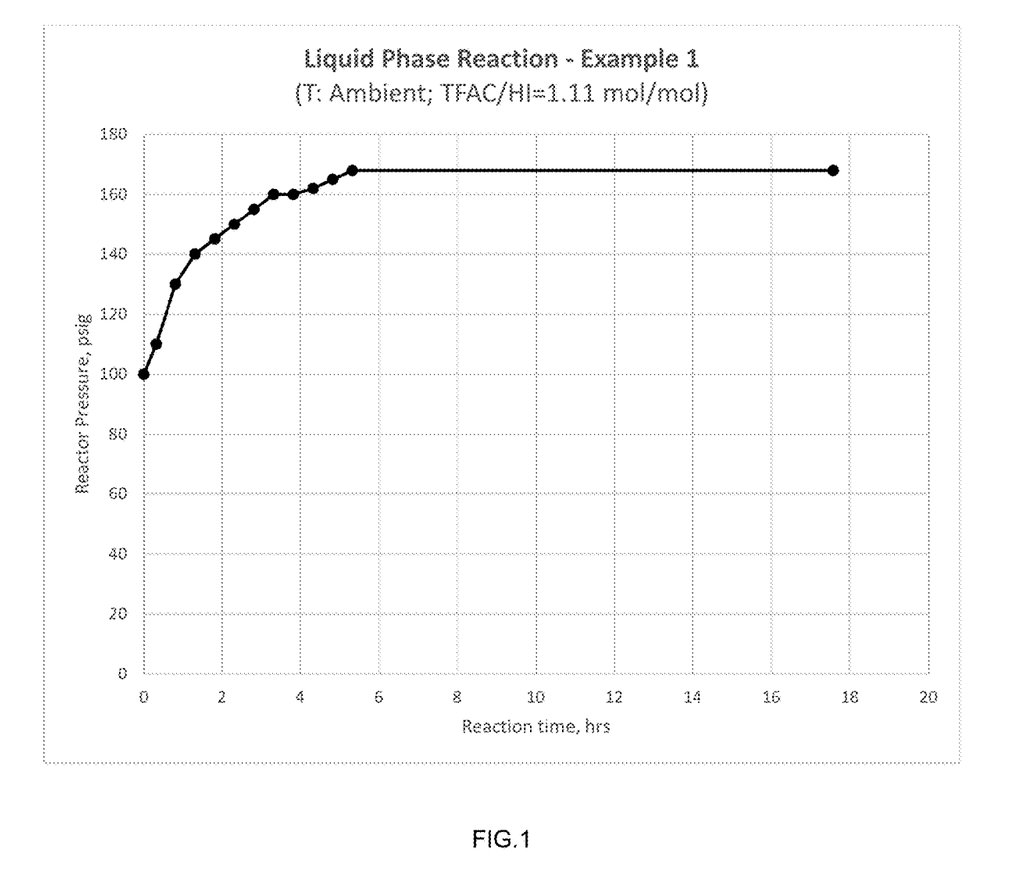
FIG. 1 corresponds to Example 1 and shows reactor pressure versus time for the liquid phase synthesis of trifluoroacetyl iodide (TFAI) at ambient temperature.

At ambient temperature, 19.94 grams of HI and 22.97 grams of TFAC (TFAC/HI molar ratio of 1.11:1.00) were charged into a 100 mL 316L reactor equipped with a pressure gauge without agitation. The cylinder pressure was monitored to track the progress of the reaction with the pressure profile as shown in FIG. 1. After 5.3 hours, the reactor pressure was stabilized at 168 psig. After 17.5 hours, the reactor was drained, and the liquid sample was analyzed by gas chromatography (GC). The results show 76.04% conversion of TFAC, and 99.99% selectivity for TFAI. No $CF_3I$ formation was observed.

Example 2

Liquid Phase Synthesis of Trifluoroacetyl Iodide (TFAI) at Ambient Temperature

Figure 2:
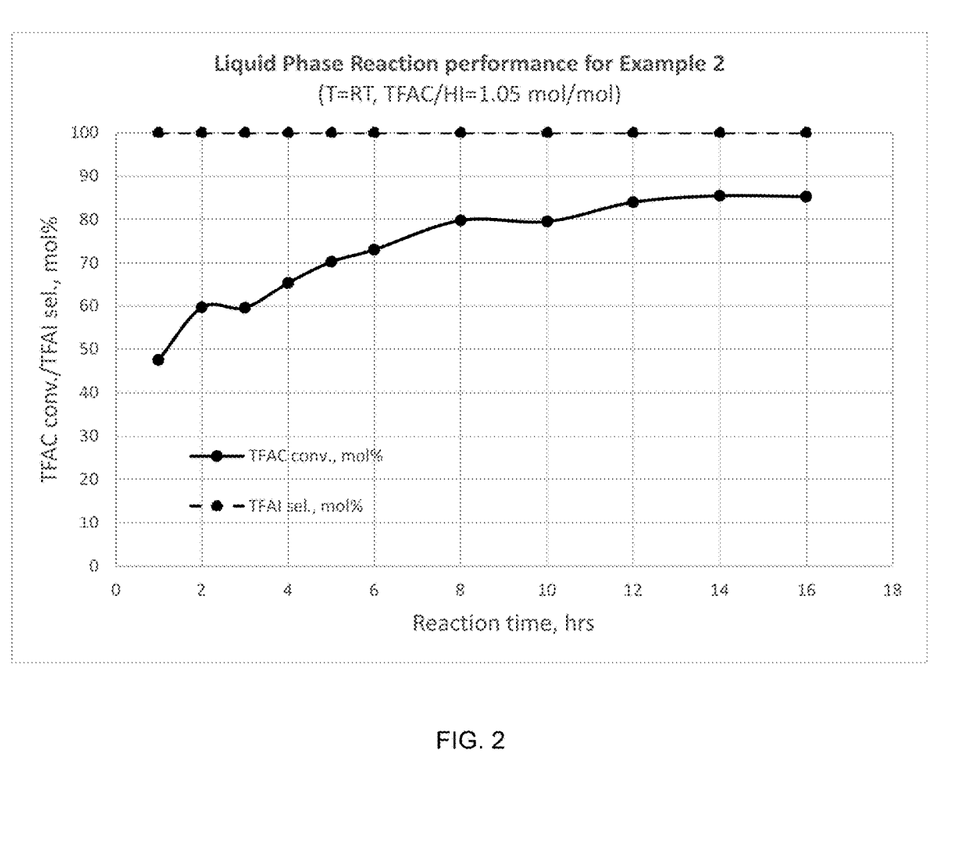
FIG. 2 corresponds to Example 2 and shows conversion of TFAC and selectivity for TFAI versus reaction time at ambient temperature.

At ambient temperature, 19.48 grams of HI and 21.21 grams of TFAC (TFAC/HI molar ratio of 1.05:1.00) were charged into a 100 mL 316L reactor equipped with a pressure gauge without agitation. Periodically, a small amount of liquid sample was drained and analyzed by gas chromatography (GC) to track the progress of the reaction with the TFAC conversion and TFAI selectivity as shown in FIG. 2. The results show that, during the first 12 hours, TFAC conversion was increased with increasing reaction time, reaching about 85.4% after 14 hours. Near 100% selectivity for TFAI was observed throughout the entire run. No $CF_3I$ formation was observed.

Example 3

Liquid Phase Synthesis of Trifluoroacetyl Iodide (TFAI) at Ambient Temperature

Figure 3:
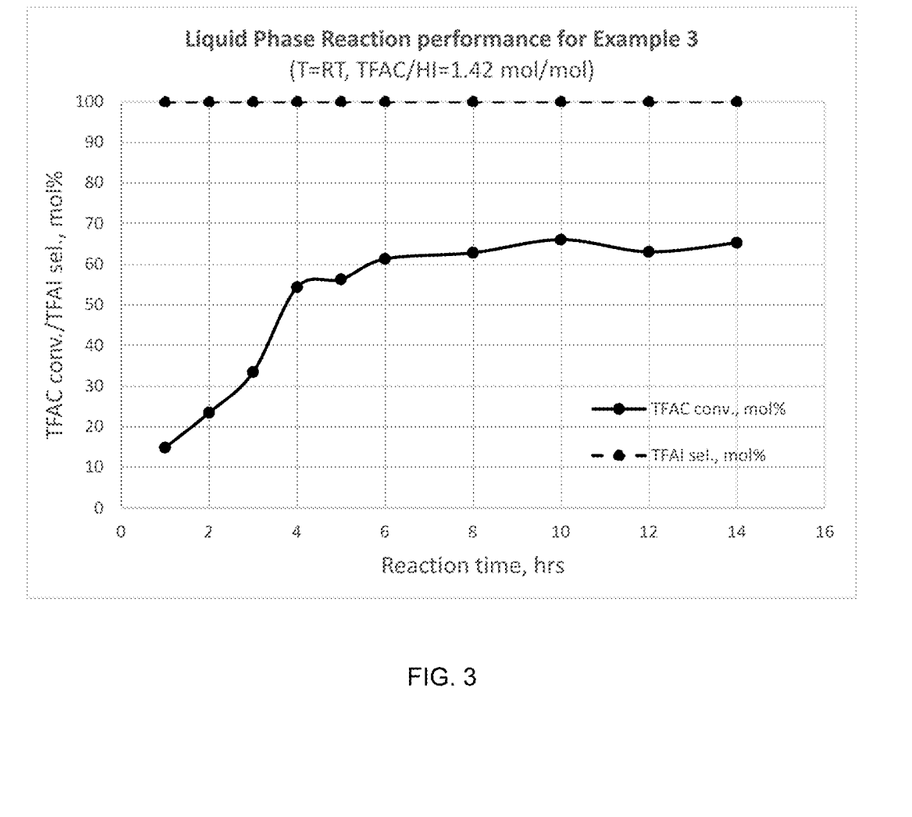
FIG. 3 corresponds to Example 3 and shows conversion of TFAC and selectivity for TFAI versus reaction time at ambient temperature.

At ambient temperature, 47.71 grams of HI and 70.30 grams of TFAC (TFAC/HI molar ratio of 1.42:1.00) were charged into a 300 mL Teflon-lined PARR reactor equipped with an agitator. The reactor was agitated during the test period. Periodically, a small amount of liquid sample was drained and analyzed by gas chromatography (GC) to track the progress of the reaction with the TFAC conversion and TFAI selectivity as shown in FIG. 3. After 14 hours, the reactor was drained, and the liquid samples were analyzed by GC. The analysis of the final liquid sample showed 65-66% conversion of TFAC and >99.9% selectivity for TFAI. No $CF_3I$ formation was observed.

Example 4

Liquid Phase Synthesis of Trifluoroacetyl Iodide (TFAI) at 90° C.

Figure 4:
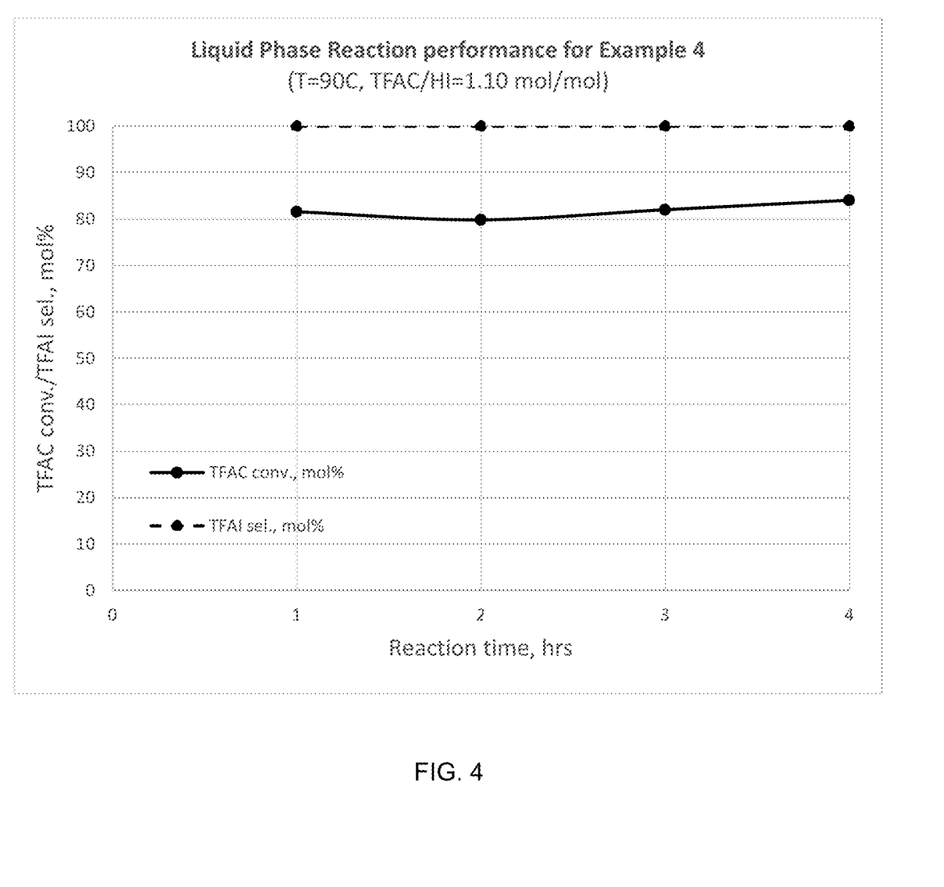
FIG. 4 corresponds to Example 4 and shows conversion of TFAC and selectivity for TFAI versus reaction time at 90° C.

A 300 mL Teflon-lined PARR reactor equipped with an agitator was charged with 64.33 grams of TFAC. The reactor was agitated and heated to 70° C., then 56.67 grams of HI was charged into the reactor (TFAC/HI molar ratio of 1.10:1.00). The reactor temperature controller was set at 90° C., with peak temperature of 98° C. observed due to exothermic reaction. Periodically, a small amount of liquid sample was drained and analyzed by gas chromatography (GC) to track the progress of the reaction with the TFAC conversion and TFAI selectivity as shown in FIG. 4. After 4 hours, the reactor was drained, and the liquid samples were analyzed by GC. The analysis of the final liquid sample showed about 84% conversion of TFAC and >99.9% selectivity for TFAI. No $CF_3I$ formation was observed.

Example 5

Liquid Phase Synthesis of Trifluoroacetyl Iodide (TFAI) at 90° C.

Figure 5:
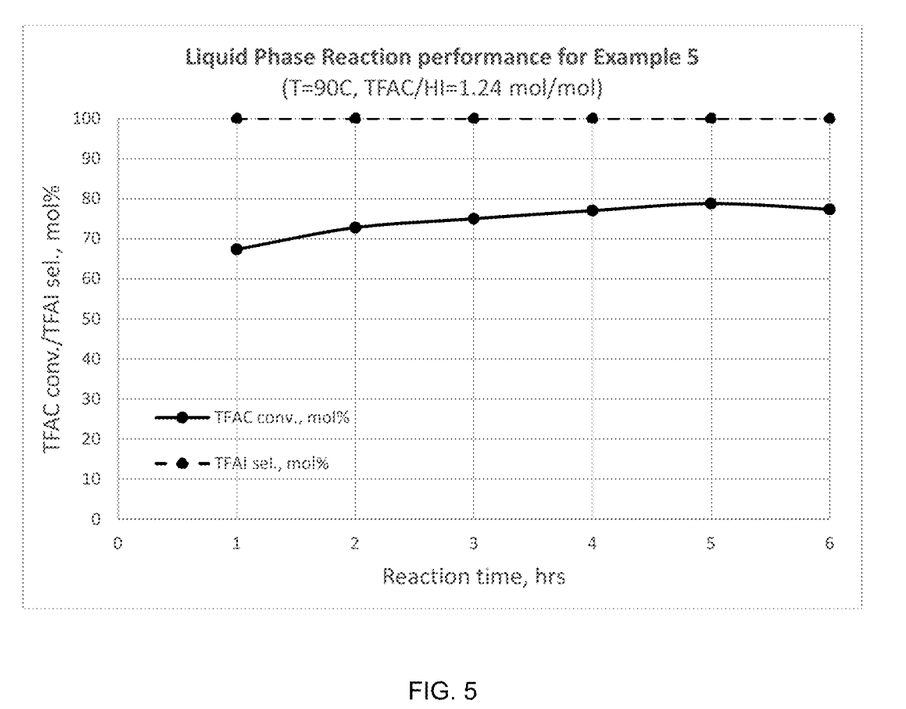
FIG. 5 corresponds to Example 5 and shows conversion of TFAC and selectivity for TFAI versus reaction time at 90° C.

A 300 mL Teflon-lined PARR reactor equipped with an agitator was charged with 65.49 grams of TFAC. The reactor was agitated and heated to 70° C., then 51.08 grams of HI was charged into the reactor (TFAC/HI molar ratio of 1.24:1.00). The reactor temperature controller was set at 90° C., with peak temperature of 97.7° C. observed due to the exothermic reaction. Periodically, a small amount of liquid sample was drained and analyzed by gas chromatography (GC) to track the progress of the reaction with the TFAC conversion and TFAI selectivity as shown in FIG. 5. After 6 hours, the reactor was drained, and the liquid samples were analyzed by GC. The analysis of the final liquid sample showed 77-78% conversion of TFAC and >99.9% selectivity for TFAI. No $CF_3I$ formation was observed.

Example 6

Liquid Phase Synthesis of Trifluoroacetyl Iodide (TFAI) at 60° C.

Figure 6:
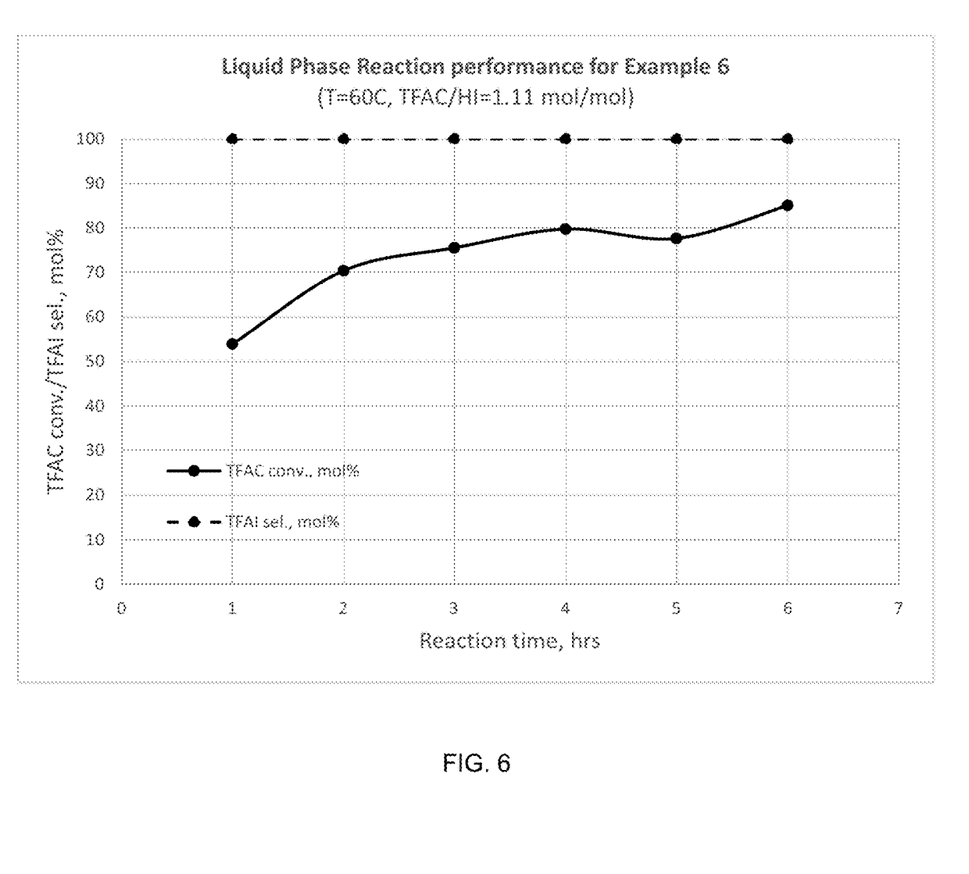
FIG. 6 corresponds to Example 6 and shows conversion of TFAC and selectivity for TFAI versus reaction time at 60° C.

A 300 mL Teflon-lined PARR reactor with agitator was charged with 70.63 grams of TFAC. The reactor was agitated and heated to 35° C., then 61.34 grams of HI was charged into the reactor (TFAC/HI molar ratio of 1.11:1.00). The reactor temperature controller was set at 60° C., with peak temperature of 61.5° C. observed due to the exothermic reaction. Periodically, a small amount of liquid sample was drained and analyzed by gas chromatography (GC) to track the progress of the reaction with the TFAC conversion and TFAI selectivity as shown in FIG. 6. After 6 hours, the reactor was drained, and the liquid samples were analyzed by GC. The analysis of the final liquid sample showed roughly 85% conversion of TFAC and >99.9% selectivity for TFAI. No $CF_3I$ formation was observed.

Example 7

Liquid Phase Synthesis of Trifluoroacetyl Iodide (TFAI) at 60° C.

Figure 7:
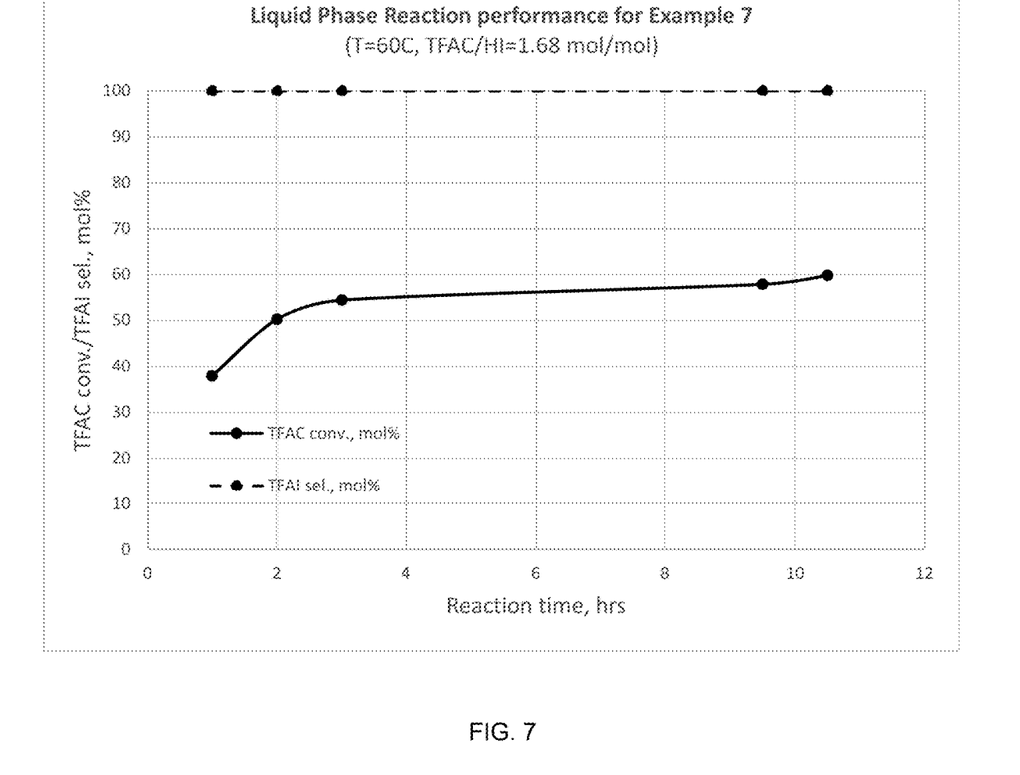
FIG. 7 corresponds to Example 7 and shows conversion of TFAC and selectivity for TFAI versus reaction time at 60° C.

A 300 mL Teflon-lined PARR reactor equipped with an agitator was charged with 74.18 grams of TFAC. The reactor was agitated and heated to 35° C., then 42.58 grams of HI was charged into the reactor (TFAC/HI molar ratio of 1.68:1.00). The reactor temperature controller was set at 60° C., with peak temperature of 65° C. observed due to the exothermic reaction. Periodically, a small amount of liquid sample was drained and analyzed by gas chromatography (GC) to track the progress of the reaction with the TFAC conversion and TFAI selectivity as shown in FIG. 7. After 10.5 hours, the reactor was drained, and the liquid samples were analyzed by GC. The analysis from the final liquid sample showed roughly 60% conversion of TFAC and near 100% selectivity for TFAI. No $CF_3I$ formation was observed.

Example 8

Liquid Phase Synthesis of Trifluoroacetyl Iodide (TFAI) at 60° C.

Figure 8:
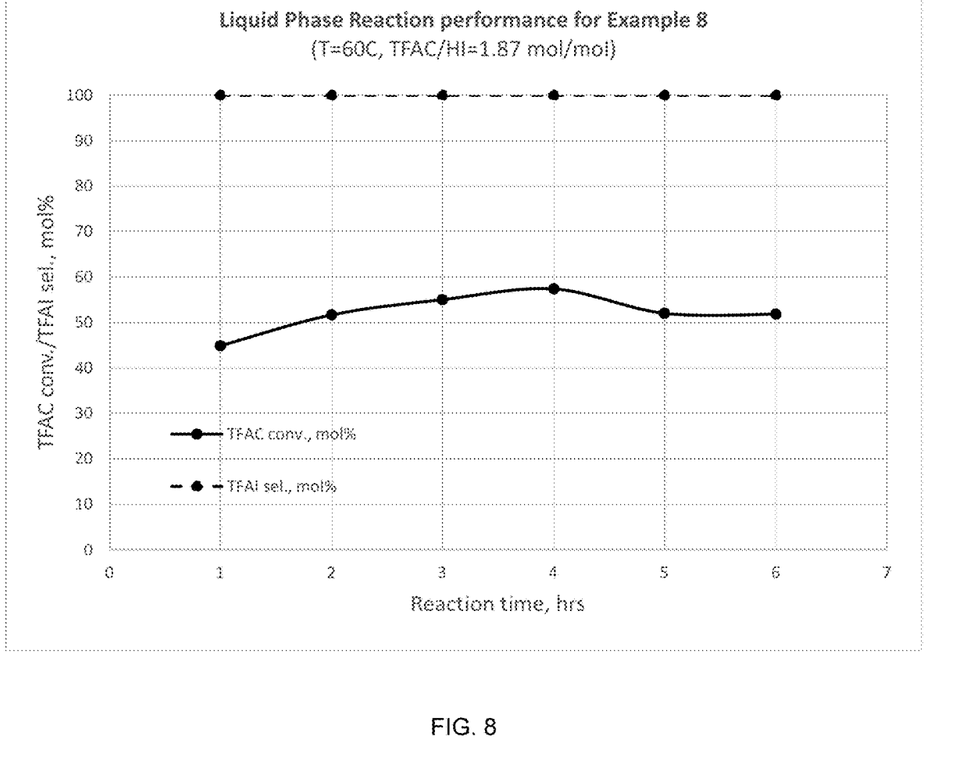
FIG. 8 corresponds to Example 8 and shows conversion of TFAC and selectivity for TFAI versus reaction time at 60° C.

A 300 mL Teflon-lined PARR reactor equipped with an agitator was charged with 75.10 grams of TFAC. The reactor was agitated and heated to 35° C., then 38.77 grams of HI was charged into the reactor (TFAC/HI molar ratio of 1.87:1.00). The reactor temperature controller was set at 60° C., with peak temperature of 66.3° C. observed due to exothermic reaction. Periodically, a small amount of liquid sample was drained and analyzed by gas chromatography (GC) to track the progress of the reaction with the TFAC conversion and TFAI selectivity shown in FIG. 8. After 6 hours, the reactor was drained, and the liquid samples were analyzed by GC. The analysis of the final liquid sample showed 51-52% conversion of TFAC and near 100% selectivity for TFAI. No $CF_3I$ formation was observed.

Example 9

Liquid Phase Synthesis of Trifluoroacetyl Iodide (TFAI) at 120° C.

Figure 9:
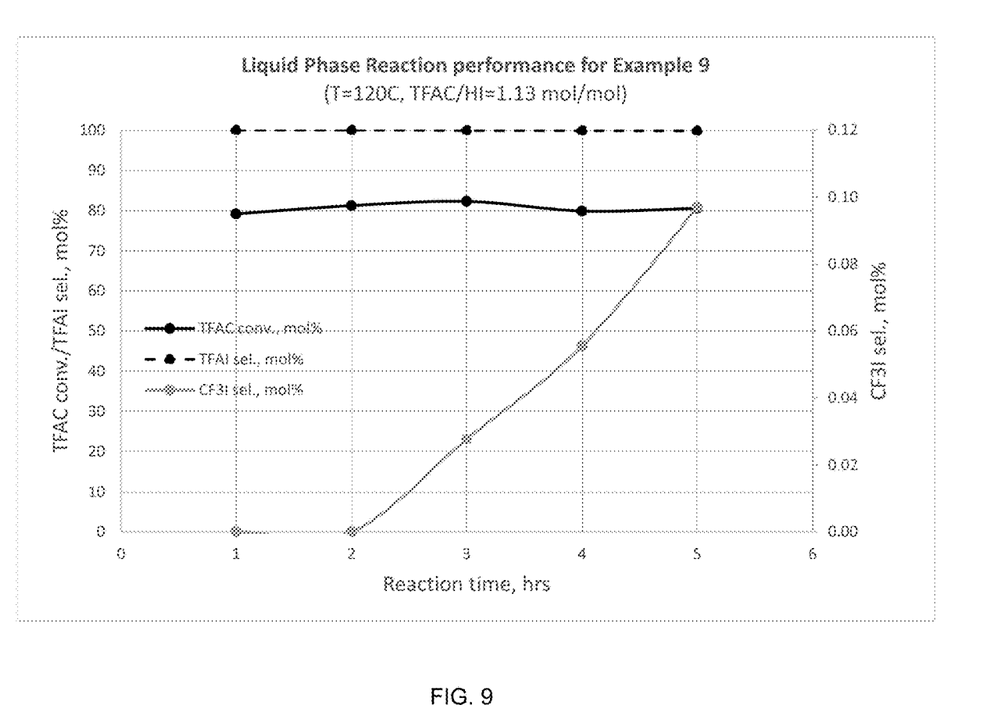
FIG. 9 corresponds to Example 9 and shows conversion of TFAC and selectivity for TFAI versus reaction time at 120° C.

A 300 mL Teflon-lined PARR reactor equipped with an agitator was charged with 65.60 grams of TFAC. The reactor was agitated and heated to 85° C., then 56.12 grams of HI was charged into the reactor (TFAC/HI molar ratio of 1.13:1.00). The reactor temperature controller was set at 120° C., with peak temperature of 121.3° C. observed due to the exothermic reaction. Periodically, a small amount of liquid sample was drained and analyzed by gas chromatography (GC) to track the progress of the reaction with the TFAC conversion and TFAI selectivity as shown in FIG. 9. After 5 hours, the reactor was drained, and the liquid samples were analyzed by GC. The analysis of the final liquid sample showed 80-81% conversion of TFAC, 99.79% selectivity for TFAI, and 0.10% selectivity for $CF_3I$.

Example 10

Liquid Phase Synthesis of Trifluoroacetyl Iodide (TFAI) at 120° C.

Figure 10:
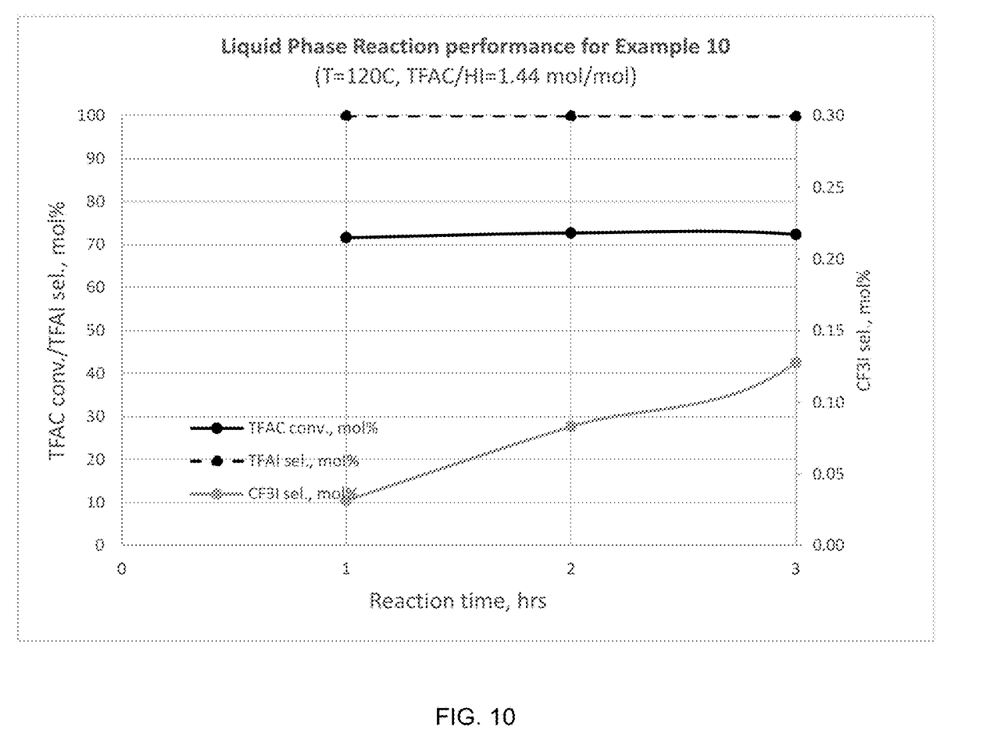
FIG. 10 corresponds to Example 10 and shows conversion of TFAC and selectivity for both TFAI and $CF_3I$ versus reaction time at 120° C.

A 300 mL Teflon-lined PARR reactor equipped with an agitator was charged with 61.08 grams of TFAC. The reactor was agitated and heated to 85° C., then 40.99 grams of HI was charged into the reactor (TFAC/HI molar ratio of 1.44:1.00). The reactor temperature controller was set at 120° C., with peak temperature of 120.9° C. observed due to the exothermic reaction. Periodically, a small amount of liquid sample was drained and analyzed by gas chromatography (GC) to track the progress of the reaction with the TFAC conversion and TFAI selectivity as shown in FIG. 10. After 3 hours, the reactor was drained, and the liquid samples were analyzed by GC. The analysis of the final liquid sample showed 72-73% conversion of TFAC, 99.82% selectivity for TFAI, and 0.13% selectivity for $CF_3I$.

Example 11

Figure 11:
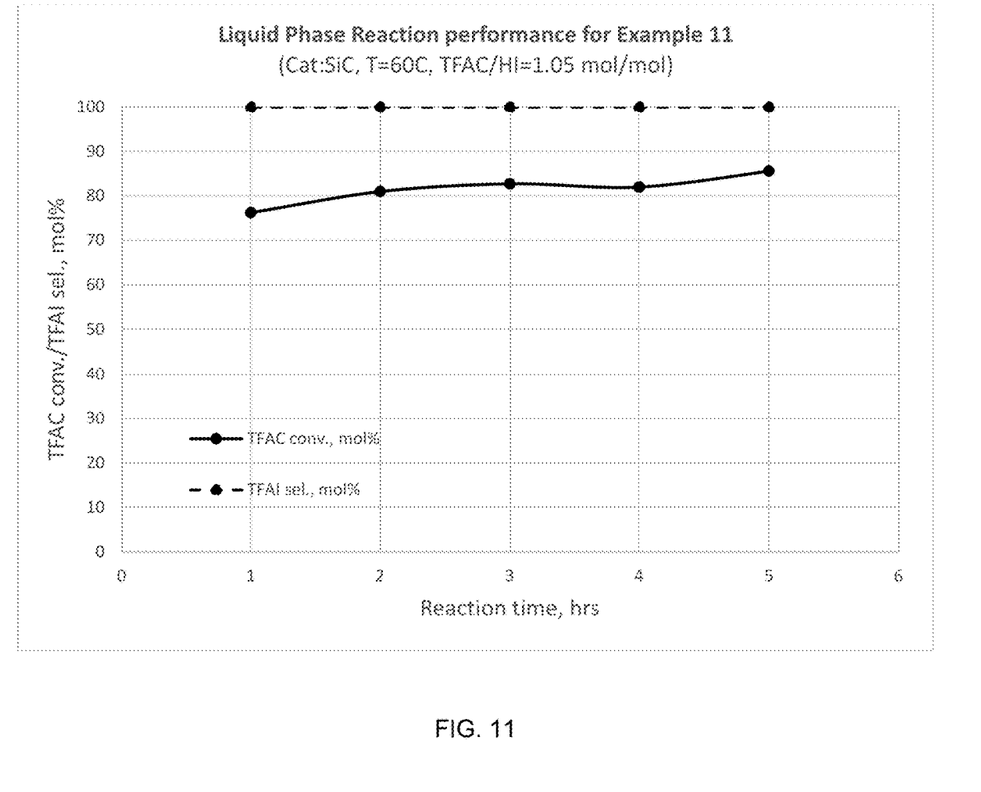
FIG. 11 corresponds to Example 11 and shows conversion of TFAC and selectivity for TFAI versus reaction time at 60° C. in the presence of a catalyst.

Liquid Phase Synthesis of Trifluoroacetyl Iodide (TFAI) with Catalyst 1.13 grams of silicon carbide (SiC) catalyst and 71.44 grams of TFAC were charged into a 300 mL Teflon-lined PARR reactor equipped with an agitator. The weight ratio of the catalyst to the TFAC was 0.016:1.00. The reactor was agitated and heated to 35° C., then 65.39 grams of HI was charged into the reactor (TFAC/HI molar ratio of 1.05:1.00). The reactor temperature controller was set at 60° C., with peak temperature of 60.2° C. observed due to the exothermic reaction. Periodically, a small amount of liquid sample was drained and analyzed by gas chromatography (GC) to track the progress of the reaction with the TFAC conversion and TFAI selectivity shown in FIG. 11. After 5 hours, the reactor was drained, and the liquid samples were analyzed by GC. The analysis of the final liquid sample showed 85-86% conversion of TFAC and 99.9% selectivity for TFAI. No $CF_3I$ formation was observed.

Example 12

Figure 12:
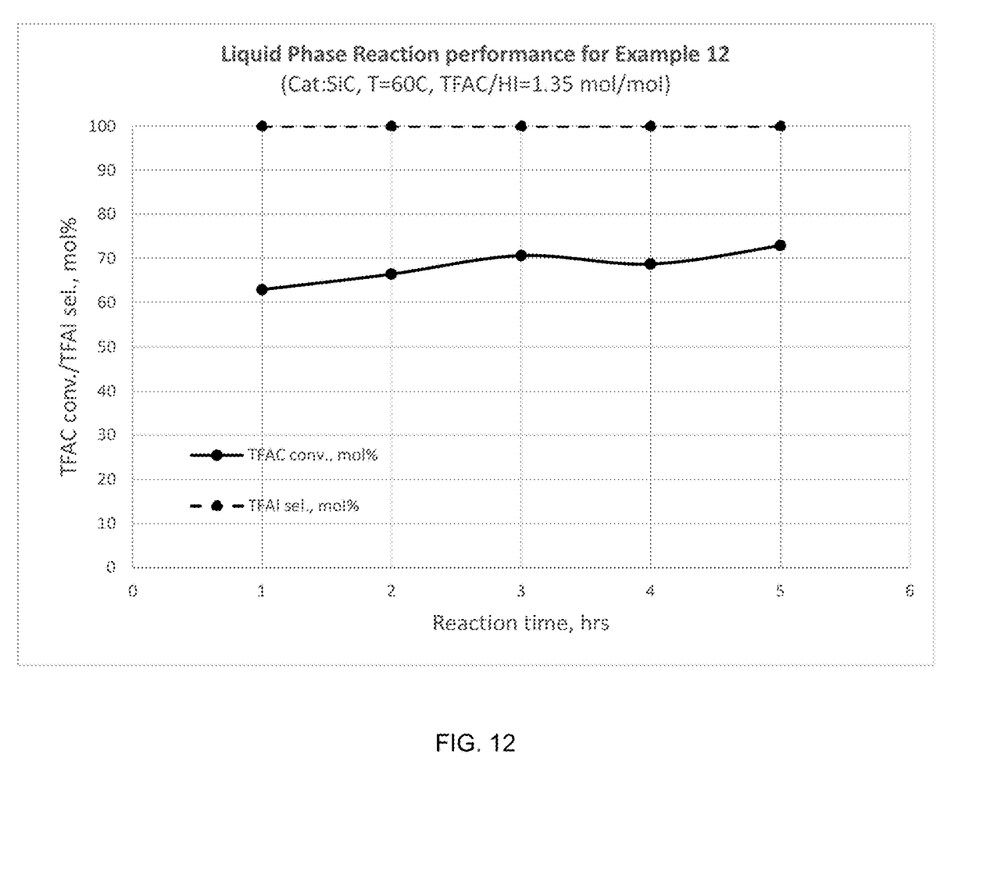
FIG. 12 corresponds to Example 12 and shows conversion of TFAC and selectivity for TFAI versus reaction time at 60° C. in the presence of a catalyst.

Liquid Phase Synthesis of Trifluoroacetyl Iodide (TFAI) with Catalyst 1.09 grams of silicon carbide (SiC) catalyst, and 74.95 grams of TFAC were charged into a 300 mL Teflon-lined PARR reactor equipped with an agitator. The weight ratio of the catalyst to the TFAC was 0.014:1.00. The reactor was agitated and heated to 35° C., then 53.80 grams of HI was charged into the reactor (TFAC/HI molar ratio of 1.35:1.00). The reactor temperature controller was set at 60° C., with peak temperature of 60.9° C. observed due to the exothermic reaction. Periodically, a small amount of liquid sample was drained and analyzed by gas chromatography (GC) to track the progress of the reaction with the TFAC conversion and TFAI selectivity shown in FIG. 12. After 5 hours, the reactor was drained, and the liquid samples were analyzed by GC. The analysis of the final liquid sample showed 72-73% conversion of TFAC and >99.9% selectivity for TFAI. No $CF_3I$ formation was observed.

Example 13

Figure 13:
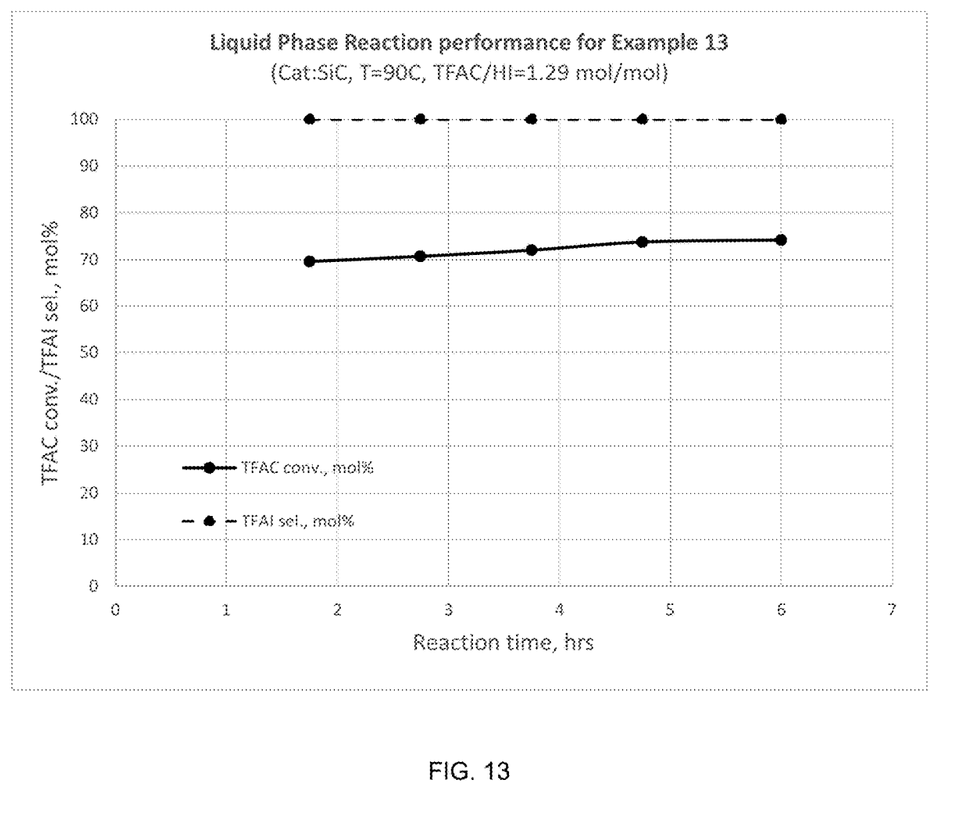
FIG. 13 corresponds to Example 13 and shows conversion of TFAC and selectivity for TFAI versus reaction time at 90° C. in the presence of a catalyst.

Liquid Phase Synthesis of Trifluoroacetyl Iodide (TFAI) with Catalyst 1.10 grams of silicon carbide (SiC) catalyst, and 76.26 grams of TFAC were charged into a 300 mL Teflon-lined PARR reactor equipped with an agitator. The weight ratio of the catalyst to the TFAC was 0.014:1.00. The reactor was agitated and heated to 75° C., then 57.12 grams of HI was charged into the reactor (TFAC/HI molar ratio of 1.29:1.00). The reactor temperature controller was set at 90° C., with peak temperature of 107.3° C. observed due to exothermic reaction. Periodically, a small amount of liquid sample was drained and analyzed by gas chromatography (GC) to track the progress of the reaction with the TFAC conversion and TFAI selectivity shown in FIG. 13. After 6 hours, the reactor was drained, and the liquid samples were analyzed by GC. The analysis of the final liquid sample showed 74-75% conversion of TFAC and >99.9% selectivity for TFAI. No $CF_3I$ formation was observed.

Example 14

Liquid Phase Synthesis of Trifluoroacetyl Iodide (TFAI)

Hydrogen iodide (172.7 grams) and 20.0 grams of TFAC (TFAC/HI molar ratio of 1.0:9.0) are charged into a 100 mL 316L reactor equipped with a pressure gauge without agitation. Periodically, a small amount of liquid sample is drained and analyzed by gas chromatography (GC) to track the progress of the reaction with the TFAC conversion and TFAI selectivity. After a time, the reactor is drained, and the liquid samples are analyzed by GC.

Example 15

Liquid Phase Synthesis of Trifluoroacetyl Iodide (TFAI)

Hydrogen iodide (20.0 grams) and 165.6 grams of TFAC (TFAC/HI molar ratio of 8.0:1.0) are charged into a 100 mL 316L reactor equipped with a pressure gauge without agitation. Periodically, a small amount of liquid sample is drained and analyzed by gas chromatography (GC) to track the progress of the reaction with the TFAC conversion and TFAI selectivity. After a time, the reactor is drained, and the liquid samples are analyzed by GC.

Example 16

Liquid Phase Synthesis of Trifluoroacetyl Iodide (TFAI) at 200° C.

A 300 mL Teflon-lined PARR reactor equipped with an agitator is charged with 61.08 grams of TFAC. The reactor is agitated and heated up to 180° C., then 40.99 grams of HI is charged into the reactor (TFAC/HI molar ratio of 1.44:1.00). The reactor temperature controller is set at 200° C. Periodically, a small amount of liquid sample is drained and analyzed by gas chromatography (GC) to track the progress of the reaction with the TFAC conversion and TFAI selectivity. After a time, the reactor is drained, and the liquid samples are analyzed by GC.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances that fall within the scope of the appended claims.

Aspects

Aspect 1 is a process for producing trifluoroacetyl iodide (TFAI), the process comprising: providing trifluoroacetyl chloride, hydrogen iodide, and an optional catalyst; and reacting the trifluoroacetyl chloride and hydrogen iodide to provide trifluoroacetyl iodide.

Aspect 2 is the process of Aspect 1, wherein in the providing step, the mole ratio of the trifluoroacetyl chloride to the hydrogen iodide is from about 1:10 to about 10:1.

Aspect 3 is the process of either of Aspect 1 or Aspect 2, wherein in the providing step, a weight ratio of the catalyst to the trifluoroacetyl chloride is from about 0.001:1 to about 0.5:1.

Aspect 4 is the process of any one of Aspects 1-3, wherein the catalyst is selected from the group consisting of silicon carbide, activated carbon, carbon molecular sieves, and combinations thereof.

Aspect 5 is the process of any one of Aspects 1-4, wherein in the reacting step, the trifluoroacetyl chloride, the hydrogen iodide, and the optional catalyst are at a temperature from 0° C. to 200° C.

Aspect 6 is a process for producing trifluoroacetyl iodide (TFAI), the process comprising: mixing trifluoroacetyl chloride, hydrogen iodide, and an optional catalyst; and heating the trifluoroacetyl chloride, hydrogen iodide, and an optional catalyst to produce trifluoroacetyl iodide and hydrogen chloride.

Aspect 7 is the process of Aspect 6, further including separating the trifluoroacetyl iodide from the hydrogen chloride, trifluoroacetyl chloride, and hydrogen iodide.

Aspect 8 is the process of either of Aspect 6 or Aspect 7, wherein the process is a continuous process.

Aspect 9 is the process of either of Aspect 6 or Aspect 7, wherein the process is a batch process.

Aspect 10 is the process of any one of Aspects 6-9, wherein the catalyst is selected from the group consisting of silicon carbide, activated carbon, carbon molecular sieves, and combinations thereof.

Aspect 11 is the process of any one of Aspects 6-10, wherein in the reacting step, the trifluoroacetyl chloride, the hydrogen iodide, and the optional catalyst are at a temperature from 0° C. to 200° C.

Aspect 12 is the process of any one of Aspects 6-11, wherein in the reacting step, the trifluoroacetyl chloride, the hydrogen iodide, and the optional catalyst are at a pressure of 5 psig to 500 psig.

The invention claimed is:

1. A process for producing trifluoroacetyl iodide (TFAI) in a liquid phase reaction, the process comprising:
providing trifluoroacetyl chloride, hydrogen iodide, and an optional catalyst;
reacting the trifluoroacetyl chloride and hydrogen iodide to provide trifluoroacetyl iodide at a temperature from 25° C. to 90° ° C.,
and
wherein the process has a selectivity for trifluoroacetyl iodide that is greater than 90%.

2. The process of claim 1, wherein in the providing step, the mole ratio of the trifluoroacetyl chloride to the hydrogen iodide is from about 1:1 to about 10:1.

3. The process of claim 1, wherein in the providing step, a weight ratio of the catalyst to the trifluoroacetyl chloride is from about 0.001:1 to about 0.5:1.

4. The process of claim 1, wherein the catalyst is selected from the group consisting of silicon carbide, activated carbon, carbon molecular sieves, and combinations thereof.

5. The process of claim 1, wherein in the reacting step, the trifluoroacetyl chloride, the hydrogen iodide, and the optional catalyst are at a temperature from 35° C. to 60° C.

6. A process for producing trifluoroacetyl iodide (TFAI) in a liquid phase reaction, the process comprising:
mixing trifluoroacetyl chloride, hydrogen iodide, and an optional catalyst; and
heating the trifluoroacetyl chloride, hydrogen iodide to a temperature from 25° C. to 90° C., and an optional catalyst to produce trifluoroacetyl iodide and hydrogen chloride, and
separating the trifluoroacetyl iodide from the hydrogen chloride, trifluoroacetyl chloride, and hydrogen iodide,
wherein the process has a selectivity for trifluoroacetyl iodide that is greater than 90%.

7. The process of claim 6, wherein the process is a batch process.

8. The process of claim 6, wherein the catalyst is selected from the group consisting of silicon carbide, activated carbon, carbon molecular sieves, and combinations thereof.

9. The process of claim 6, wherein in the heating step, the trifluoroacetyl chloride, the hydrogen iodide, and the optional catalyst are at a temperature from 35° C. to 60° C.

10. The process of claim 6, wherein in the heating step, the trifluoroacetyl chloride, the hydrogen iodide, and the optional catalyst are at a pressure of 5 psig to 500 psig.

11. The process of claim 1, wherein in the reacting step, the trifluoroacetyl chloride, the hydrogen iodide, and the optional catalyst, are at a temperature from 25° C. to 90° C., and the process results in a greater than 80% conversion of trifluoroacetyl chloride and a greater than 99% selectivity for TFAI.

12. The process of claim 1, wherein in the reacting step, the trifluoroacetyl chloride, hydrogen iodide, and the optional catalyst, have a residence time from about 0.1 hours to about 5 hours to provide trifluoroacetyl iodide.

13. The process of claim 1, wherein the process is a continuous process.

14. The process of claim 1, wherein a catalyst is present and where the catalyst is silicon carbide.

15. The process of claim 6, wherein the process results in a greater than 80% conversion of trifluoroacetyl chloride and a greater than 99% selectivity for TFAI.

* * * * *